United States Patent
Jessberger et al.

(10) Patent No.: US 9,012,372 B2
(45) Date of Patent: Apr. 21, 2015

(54) METHOD AND MEANS FOR IDENTIFYING SUBSTANCES WHICH INHIBIT IGE PRODUCTION

(75) Inventors: Rolf Jessberger, Dresden (DE); Tatsiana Audzevich, London (GB)

(73) Assignee: Albonia Biotech, Inc., Vancouver (CA)

( * ) Notice: Subject to any disclaimer, the term of this patent is extended or adjusted under 35 U.S.C. 154(b) by 0 days.

(21) Appl. No.: 13/640,928

(22) PCT Filed: Apr. 14, 2011

(86) PCT No.: PCT/EP2011/055942
§ 371 (c)(1),
(2), (4) Date: Oct. 12, 2012

(87) PCT Pub. No.: WO2011/141267
PCT Pub. Date: Nov. 17, 2011

(65) Prior Publication Data
US 2013/0035280 A1    Feb. 7, 2013

(30) Foreign Application Priority Data
Apr. 15, 2010  (DE) .................. 10 2010 027 827

(51) Int. Cl.
| C40B 30/04 | (2006.01) |
| A61K 51/00 | (2006.01) |
| A61M 36/14 | (2006.01) |
| C12Q 1/68 | (2006.01) |
| G01N 33/53 | (2006.01) |
| G01N 33/00 | (2006.01) |
| G01N 33/564 | (2006.01) |
| G01N 33/563 | (2006.01) |
| A61K 38/00 | (2006.01) |

(52) U.S. Cl.
CPC .......... *G01N 33/564* (2013.01); *G01N 2500/02* (2013.01); *G01N 2800/24* (2013.01)

(58) Field of Classification Search
None
See application file for complete search history.

(56) References Cited

U.S. PATENT DOCUMENTS

| 6,528,284 B1 | 3/2003 | Wabl et al. | |
| 2003/0166018 A1* | 9/2003 | Wabl et al. | .............. 435/7.21 |

OTHER PUBLICATIONS

Oettgen, H., "Regulation of the IgE isotype switch: new insights on cytokine signals and the functions of epsilon germline transcripts," Curr. Opin. Immunol. 12:618-623 (2000).*

Qi et al., "Differential regulation of germinal center genes, BCL6 and SWAP-70, during the course of MAIDS," Molec. Immunol. 36:1043-1053 (1999).*

Borggrefe T et al: Impaired IgE response in SWAP-70-definient mice; Eur. J. Immunol. 2001, 31: pp. 2467-2475 (Aug. 2001)—see international search report.

Sivalenka R R et al: SWAP-70 regulates mast cell FCepsilonRl-mediated signaling and anaphylaxis; Eur. J. Immunol. 2008, 38: pp. 841-854 (Mar. 2008)—see international search report.

Hellman L: Regulation of IgE homeostasis, and the identification of potential targets for therapeutic intervention; Biomedicine & Pharamcotherapy 61 (2007) pp. 34-49 (Feb. 2, 2007)—see international search report.

Oettgen H C: Regulation of the IgE isotype switch: new insights on cytokine signals and the function of epsilon germline transcripts; Current Opinion in Immunology 2000, 12: pp. 618-623 (Dec. 1, 2000)—see international search report.

Borggrefe T et al: A B-cell-specific DNA Recombination Complex; The Journal of Biological Chemistry; vol. 273, No. 27; pp. 17025-17025 (Jul. 3, 1998); mentioned in specification, p. 1, last paragraph.

Borggrefe T et al: Cellular, intracellular, and developmental expression patterns of murine SWAP-70; Eur. J. Immunol. 1999, 29: pp. 1812-1822; mentioned in specification, p. 1, last paragraph.

Gross B et al: SWAP-70-deficient mast cells are impaired in development and IgE-mediated degranulation; Eur. J. Immunol. 2002, 32: pp. 1121-1128; mentioned in specification, p. 1, last paragraph.

Pearce G et al: Signaling Protein SWAP-70 is required for efficient B cell homing to lymphoid organs; Nature Immunology Advance Online Publication Jul. 16, 2006—doi:10.1038/ni1365; mentioned in specification, p. 1, last paragraph.

Ocana-Morgner C et al: SWAP-70 regulates RhoA/RhoB dependent MHCII surface localization in dendritic cells ; Blood; 2009, 113: pp. 1474-1482; prepublished online Sep. 18, 2008; mentioned in specification, p. 1, last paragraph.

Masat L et al: Association of SWAP-70 with the B cell antigen receptor complex:PNAS (Feb. 29, 2000) vol. 97, No. 5, pp. 2180-2184; mentioned in specification, p. 1, last paragraph.

* cited by examiner

*Primary Examiner* — James H Alstrum Acevedo
*Assistant Examiner* — Thea D'Ambrosio
(74) *Attorney, Agent, or Firm* — Gudrun E. Huckett (57) ABSTRACT

The invention relates to the field of biomedical and pharmacological research, in particular to the area of immunology, allergies and autoimmune diseases. The inventors have shown that SWAP-70 is a higher-level regulator for STAT-6 and BCL-6, the regulator being specific for IgE production in B-cells by amplifying the effect of STAT-6 and antagonizing the effect of BCL-6. The inventors have observed no influence of SWAP-70 on the expression of other genes that are likewise regulated by STAT-6 and/or BCL-6. In summary, it can be concluded that SWAP-70 positively regulates IgE production by shifting the interaction of the two antagonists STAT-6 and BCL-6 with regulatory elements of the IgE gene in favor of the activator STAT-6. Based on said findings, the invention provides a screening method which allows for identifying novel active agents that specifically inhibit IgE production. The substances identified by the method according to the invention are particularly suited for treating IgE-induced allergies and IgE-dependent autoimmune diseases.

6 Claims, 6 Drawing Sheets

METHOD AND MEANS FOR IDENTIFYING SUBSTANCES WHICH INHIBIT IGE PRODUCTION

BACKGROUND OF THE INVENTION

The invention concerns the field of biomedical and pharmacological research, in particular in the field of immunology, allergies, and autoimmune diseases.

STATE OF THE ART

Allergies, also including asthma, and autoimmune diseases are diseases that are very widespread worldwide and on the rise, wherein allergies can cause death in severe cases. The incidence of allergies has tripled during the last 20 years. Between 5 and 10 of the world population suffer from allergies, including asthma, with about one fifth of said people suffering from asthma. Asthma is the most frequent chrome illness in those younger than 18. Allergies are triggered by excessive IgE production of the B-lymphocytes. Interventions in the regulation of this IgE production are therefore in principle groundbreaking for a causal allergy therapy which does not exist up to now. However, up to now too little is known about how the IgE production is regulated in detail.

The IgE production depends, as has been known for a long time, on the transcription-activating function of the protein STAT-6. It is also know that the effect of STAT-6 on the IgE production is inhibited by BCL-6. BCL-6 and STAT-6 bind an overlapping region of the regulatory DNA sequence of the IgE gene. It is assumed that BCL-6 interacts with co-repressors and thereby inhibits actively the IgE production. This repression is specific for the IgE gene, because BCL-6 binds selectively to the STAT-6 binding site in the IgE gene and does not bind to most of the other STAT-6 binding sites. Nevertheless, the exact mechanisms of specificity and regulation of the critical balance between BCL-6 and STAT-6 are not known.

The SWAP-70 protein is expressed mainly in activated B-cells, in mast cells, and in dendritic cells, although the presence of the protein in the cytoplasm of other cell types cannot be excluded (Borggrefe et al. 1998; Borggrefe et al. 1999; Masat et al, 2000; Gross et al, 2002; Pearce et al, 2006; Ocana-Morgner et al. 2009). It is known that SWAP-70 deficient mice exhibit special modifications of the phenotype, inter alia the CD40-mediated activation of B-cells, including the change to the production of IgE, and the degranulation of mast cells is strongly reduced (Borggrefe et al, 2001; Gross et al. 2002). Concerning the IgE production as a function of SWAP-70, it has been shown that in SWAP-70 deficient mice greatly decreased IgE concentrations are present prior to and after immunization, and that the production of secreted IgE in B-cell cultures is reduced approximately 8-fold. Nevertheless, the production of other immunoglobulin classes is not affected substantially.

In U.S. Pat. No. 6,528,284 B1 (US2003/143611A1), purification and characterization of proteins which are involved in general in immunoglobulin class switching are discussed, SWAP-70 was identified which is referred to here as SRTA-70 (S-region transfer activity-70) and is claimed. Its general role in immunoglobulin class switching is described, as well as the use of this protein in the modulation of the class switch.

The role of SWAP-70 is described in US 2003/0166018 A1 in mast cell degranulation; a method for identifying in agent which reduces the content of SWAP-70 protein in a mast cell is claimed.

Nowadays, the allergy treatment occurs predominantly with the aid of symptom treatment, i.e. relief of the allergic reaction, for example, through anti-histamines or glucocorticoids, but not through causal therapy. Disadvantages of present therapies are inter aha a short-time effect, no elimination of the cause, unspecific effect and side effects.

The only presently known IgE-inhibitor is omalizumab, a recombinant humanized monoclonal antibody against immunoglobulin E (anti-IgE) for the treatment of severe allergic bronchial asthma. But even omalizumab does not inhibit causally the IgE production, but rather intercepts already produced IgE so that immunoglobulin complexes are generated. Disadvantageously, antibody therapies themselves can trigger allergic reactions or immunoreactions that attack the antibody protein. Besides, the pharmacological production of antibodies is complex.

OBJECT OF DIE INVENTION

The object of the invention is therefore to provide a method which enables screening in a targeted fashion for active substances that can be used as new anti-allergic agents and that inhibit in particular the production of IgE. Moreover, the invention should provide means for performing the screening method.

SUMMARY OF THE INVENTION

The invention is based on the finding that SWAP-70 regulates positively the function of STAT-6 specifically in the IgE production. In the absence of SWAP-70, a strongly reduced IgE production is found; this has been shown by the inventors in vitro and in the mouse model. Hence, the therapeutic inhibition of SWAP-70 may represent an important way of allergy therapy.

Another important finding is that SWAP-70 negatively regulates the inhibition of IgE production exercised by BCL-6. In the absence of SWAP-70, significantly more BCL-6 binds to the relevant IgE DNA region, i.e.; the IgE production is inhibited.

The effects of SWAP-70 on STAT-6 and on BCL-6 as well as on the balance between STAT-6 and BCL-6 that is critical for the IgE production have been unknown up to now.

In summary; it can be concluded that SWAP-70 regulates the IgE production positively in that it shifts the interaction of the two antagonists STAT-6 and BCL-6 with regulatory elements of the IgE gene in favor of the activator STAT-6.

The inventors have shown that SWAP-70 is a superior regulator for STAT-6 and BCl-6 which is specific for the WE production in B-cells in that it strengthens the effect of STAT-6 and antagonizes the effect of BCL-6. The inventors have observed no influence of SWAP-70 on the expression of other genes that are also regulated by STAT-6 and/or BCL-6.

Based on these findings the invention makes available a screening method which enables the identification of new active substances that inhibit specifically the IgE production.

The inhibition of the effect of SWAP-70 on STAT-6 is advantageously highly specific for the IgE production in B-cells. This enables the development of active substances that treat IgE-dependent allergies and autoimmune diseases not symptomatically as before, but causally. This is achieved in particular by active substances which inhibit the stimulating, function of SWAP-70 on STAT-6.

The method according to the invention comprises the following steps:
(i) contacting
  (a) at least one candidate substance with
  (b) SWAP-70 and
  (c) BCL-6 and/or STAT-6
(ii) selecting a candidate substance which preferably specifically inhibits the SWAP-70 mediated activation of STAT-6 and/or reinforces the BCL-6 mediated inhibition of STAT-6.

Preferably, in step (ii) a candidate substance is selected which enhances the interaction of SWAP-70 with BCL-6 and/or influences it such that the inhibiting effect of BCL-6 is reinforced.

Alternatively, a candidate substance is selected which inhibits the interaction of SWAP-70 with STAT-6.

The term interaction is to be understood preferably as a direct protein-protein interaction or also an indirect interaction mediated by other proteins, respectively.

Preferably, a candidate substance is selected which specifically inhibits SWAP-70 mediated activation of STAT-6 and/or reinforces the BCL-6 mediated inhibition of the SWAP-70 mediated activation of STAT-6 or blocks the inhibiting effect of SWAP-70 on BCL-6.

The candidate substances are preferably so-called "small molecules", i.e., compounds with a molecular weight up to 800 Daltons (atomic mass unit u). The candidate substances are preferably organic molecules or also peptides.

The interaction of the proteins SWAP-70, STAT-6 and/or BCL-6 and, if necessary, of the regulatory elements of the IgE gene is measured preferably in vitro or in situ.

In vitro (i.e., in cell-free methods), the effect of the candidate substance(s) is tested with respect to the interaction between SWAP-70 and BCL-6 and/or SWAP-70 and STAT-6 (in the following referred to together also as binding partners) preferably by using the appropriately purified proteins as a binding partner. This occurs, for example, in binding assays in which the association of a marked binding partner with an unmarked one or two differently marked binding partners is measured. Assays of this kind can be performed inter alia in multi-well methods (like ELISA) or in solution (e.g., by means of AlphaScreen) in high throughput. Markers are, e.g., fluorescent dyes which are bound covalently to one or both binding partners. Alternatively, marking occurs radioactively, by means of affinity tags, haptamers or by marking with fluorescent, proteins (preferably as a fusion protein—e.g., with GFP). The fluorescence signals remaining at the unmarked partner or the fluorescence interference between associated partners is read out.

In situ (i.e. in cells, preferably in cell culture), the effect of the candidate substance(s) on the interaction between SWAP-70 and/or SWAP-70 and STAT-6 is measured preferably in cells that express SWAP-70 and BCL-6 and/or SWAP-70 and STAT-6. Here, the detection of the interaction between the binding, partners SWAP-70 and BCL-6 and/or SWAP-70 and STAT-6 preferably occurs in cell lysates. Here, marking of the individual binding partners (SWAP-70, BCL-6 and/or STAT-6) also occurs, e.g., by means of affinity tags (e.g.; His tag) and suitable affinity binding materials (for example, $Ni^{2+}$) bonded to these materials.

The effect of cell-permeating candidate substances influences the binding partners in a similar way as described above in connection with in vitro methods. Preferably, the in situ methods are carried out with the aid of well-known, easily cultured and transfectable cell lines in which the binding partners are expressed. Suitable cell lines are, e.g., NIH3T3, 293T and COS-7. Interactions between the binding partners can be analyzed advantageously also in non-mammalian cell system, e.g., in yeast cells (Yeast2 hybrid system) or insect cells (co-precipitation after expression), or after co-translation in cell-free systems (in vitro transcription/translation systems, followed by co-precipitations, so-called pull-downs). As negative controls, preferably appropriate cells or cell lines are used in which the genes that code for individual ones of these proteins, do not exist or are deleted (e.g., cells from SWAP-70$^{-/-}$ mice, like, e.g. embryonic mouse fibroblasts). Multi-well formats permit high throughput screening methods.

Alternatively, the detection of the interaction of the binding partners can be examined in retro or also in the cell by Förster resonance energy transfer (FRET) analyses. For this purpose, two of the binding partners (preferably SWAP-70 and BCL-6 or, alternatively, SWAP-70 and STAT-6) are marked preferably with two molecules different from each other and suitable for producing FRET. These two molecules that are different from each other are referred to in the following also as FRET donor and FRET acceptor (or also simply donor and acceptor).

The Förster resonance energy transfer (briefly FRET) is a physical process in which energy of an excited donor can be transferred free of radiation onto an acceptor at a distance of about 1.5 to 10 nm. The molecules are so selected that the emission spectrum of the donor molecule overlaps with the excitation spectrum of the acceptor. When donor and acceptor are fluorescent dyes, this is referred to as fluorescence resonance energy transfer. When the donor or the acceptor, however, are a chemoluminescence or a bioluminescence source, the term chemoluminescence resonance energy transfer (CRET) or bioluminescence resonance energy transfer (BRET) is used.

For in vitro assays the donor and/or the acceptor is preferably bound to the binding partner covalently or by coordination. The marking of the protein is preferably realized covalently on free amino groups or carboxyl groups of the amino acid side chains (lysine or aspartate or glutamate residues) of the protein. Organic or inorganic fluorescent dyes are used preferably according to the invention as donors and acceptors. Preferably, from 1 to 40, particularly preferred, from 1 to 5, dye molecules are bound per protein molecule. As inorganic fluorescent dyes preferably e.g. europium (preferably $Eu^{3+}$), cerium or terbium or so-called quantum dots (quantum dots), as for example doped $LaF_3$ and $LaPO_4$ nanoparticies, are used.

Binding of a biomolecuie, such as fluorescent proteins (e.g., UP, YFP and CFP) and/or luciferase is realized either through crosslinking or through production of a fusion protein. Fusion proteins with such biomolecules permit advantageously also the detection of the interaction of the binding partners in situ (in the cell). Luminescence sources (like luciferase) and fluorescent proteins can be used advantageously as acceptors and donors.

As an alternative to cells, multicellular organisms can be also. Here, the interaction of the binding partner is preferably determined in vivo. Other multicellular organisms, are selected from vertebrates (except humans) and invertebrates, like *Drosophila melanogaster, Caenorhahditis elegans, Xenopus laevis*, Medaka, zebrafish or *Mus musculus*, or their embryos.

Preferred donor-acceptor pairs and their respective excitation maxima ($max_{ex}$) as well as emission maxima ($max_{em}$) are selected from:

| Donor | | | Acceptor | | |
|---|---|---|---|---|---|
| Name | max$_{ex}$ | max$_{em}$ | Name | max$_{ex}$ | max$_{em}$ |
| Alexa Fluor 488 | 495 nm | 519 nm | Alexa Fluor 555 (or also Alexa Fluor 546 or 568) | 555 nm | 565 nm |
| Alexa Fluor 546 | 556 nm | 573 nm | Alexa Fluor 633 | 632 nm | 647 nm |
| Alexa Fluor 555 | 555 nm | 565 nm | Alexa Fluor 647 | 650 nm | 668 nm |
| Alexa Fluor 568 | 578 nm | 603 nm | Cy5 | 649 nm | 670 nm |
| Alexa Fluor 568 (or also Cy3) | 578 nm | 603 nm | Alexa Fluor 633 (or also Cy5 or Alexa Fluor 647) | 632 nm | 647 nm |
| europium (Eu$^{3+}$) | 395 nm 466 nm | 617 nm | Allophycocyanine | 650 nm | 660 nm |
| Eu$^{3+}$ (or LaF$_3$) | 395 nm | 591 nm | Alexa Fluor 594 (or also Alexa Fluor 610 or 633) | 590 nm | 630 nm |
| LaPO$_4$ (or Ce or Tb) | 266 nm | 542 nm | Alexa Fluor 532 | 530 nm | 560 nm |
| cyan fluorescent protien (CFP) | 452 nm | 505 nm | yellow fluorescent protien (YFP) | 514 nm | 527 nm |
| luciferase | | | YFP | 514 nm | 527 nm |
| EGFP | 488 nm | 509 nm | YFP | 514 nm | 527 nm |

FRET analyses are also suitable for high throughput screening. A FRET donor is bound to one of the binding partners, a FRET acceptor to the other one, wherein the two of them together form a FRET pair. When the two binding partners are independent of each other in vitro or in the cell, no FRET occurs. Through the interaction of the two binding partners, the FRET donor and the FRET acceptor are brought into immediate vicinity and thereby FRET is triggered.

By FRET, the radiation emission and the fluorescence life span of the donors decrease and the acceptor emission increases. This results in a measurable shift of the wavelength of the emitted light in case of interaction of the binding partners which can be detected with the aid of suitable instrument-based methods. For example, fluorescence microscopes, flow cytometers, fluorimeters or plate spectrophotometers are suitable for this purpose.

The candidate substances influence the interaction of the binding partners. Preferably, candidate substances are selected which reduce the interaction of SWAP-70 with STAT-6 and/or reduce the interaction of SWAP-70 with BCL-6.

The inventors have proved (see FIGS. 4A and 4B) by chromatin immunoprecipitation (ChIP) that SWAP-70 binds in IL-4 stimulated B-cells together with STAT-6 and BCL-6 to the promoter region of the IgE gene (Iε promoter) but not to the promoter region of the IgG1 gene (γ1 promoter). SWAP-70 thereby regulates STAT-6 dependent transcription specifically at the it promoter.

Preferably, step (i) is carried out in the presence of one or several regulatory elements of the IgE gene to which STAT-6 as well as BCL-6 bind. These regulatory elements are DNA sequences which are present preferably as a double strand and contain the Iε promoter and/or the following sequences:

Iε GLT Promoter:

```
                                        (SEQ ID No. 1)
5' . . . CCCACTGTGCCTTAGTCAACTTCCCAAGAACAGAAT

CAAAAGGGAACTTCCAAGGCTGCTAAGGCCGGGGGTTCCCACCCC

ACTTTTA . . . 3'
```

The STAT-6 binding site is underlined, it is positioned at −111 to −102 relative to the start site of the GLT transcription of Iε. The −111/−102 sequence is also one of at least two binding sites for BCL-6.

The second STAT-6 binding site lies at −157 to −149:

```
Sequence:
                                        (SEQ ID No. 2)
5' . . . TGTCTCCTAGAAAGAGG . . . 3'.
```

The BCL-6 binding site is underlined.
Preferably, the regulatory elements used in the invention contain the SEQ ID Nos. 1 and 2.

Preferably, step (i) a candidate substance is selected which shifts the interaction of the two antagonists STAT-6 and BCL-6 with regulatory elements of the igE gene in favor of BLC6.

SWAP-70 controls binding of BCL-6 and STAT-6 to regulatory elements of the IgE gene. This binding action is preferably reproduced in vitro, preferably in an electrophoretic mobility shift assay EMSA (also referred to as gel shift or band shift assay) or high throughput variations thereof. Here, binding to the regulatory elements of the IgE gene (i.e. oligonucleotides preferably selected as discussed above) is tested, e.g., in the multi-well format. The effect of the candidate substance on SWAP-70 mediated binding of STAT-6 and/or BCL-6 can be proved based on the association of appropriately marked binding partner (SWAP-70, BCL-6 and/or STAT-6) and oligonucleotides. In this connection, the oligonucleotides are fixed preferably to a carrier material. Alternatively, the oligonucleotides are marked and one of the binding partners is fixed to a carrier material.

The candidate substances ascertained with the method according to the invention are preferably tested with respect to biological effectiveness, i.e. the inhibition of the IgE production. In this context, preferably B-lymphocytes are triggered in situ or in vivo to produce IgE. Preferably, isolated spleen cells (e.g., of the mouse) are used because they contain large number of B-lymphocytes. B-lymphocytes must not be purified for this purpose. The B-lymphocytes can be stimulated by means of IL-4 (preferably murine and e.g., made recombinantly) and CD40L (e.g., by fixed CD40L-expressing cells) to produce IgE. The IgE production can be measured simply and with high throughput e.g., with the help of FACS analysis or ELISA. Preferably, candidate substances are selected which reduce the IgE production.

Preferably, in order to analyze the mechanism of the effect of the candidate substances, a co-immunoprecipitations or SWAP-70 with BCL-6 or with STAT-6 from B-cells was carried out which triggers, as described above, the NE production and brought into contact with the candidate substance. By the co-immunoprecipitation it can be determined how the candidate substance influences the interaction of SWAP-70 with BCL-6 and/or with STAT-6. When the candidate substance inhibits the interaction of SWAP-70 with STAT-6, these two proteins will be co-precipitated in small quantities. When the candidate substance reinforces the interaction of SWAP with BCL-6, these two proteins are co-precipitated in increased quantity.

A very advantageous variant is the chromatin immunoprecipitation. Here, the interaction of SWAP-70. BCL-6 and/or STAT-6, preferably, of all three proteins, with regulatory elements of the IgE gene in the cell, i.e. with highly relevant material ex vivo, is determined or the influence of the candidate substance on this interaction.

The substances identified with the method according to the invention are suited in particular for the treatment of IgE-mediated allergies, in particular the treatment of IgE dependent allergic reactions or type I allergies and of autoimmune diseases that are IgE dependent. The substances identified by the methods according to the invention are suited in particular for the treatment of diseases that are dependent on IgE such as allergic asthma, allergic rhinitis, allergic conjunctivitis, allergic reactions of the gastrointestinal tract (in particular vomiting and diarrhea), neurodermatitis, psoriasis, contact eczema, urticaria, allergic edemas, in particular the larynx edema, and the angioedema (Quincke edema), anaphylactic shock, allergic vasculitis, angiitis or granulomatosis (Churg Strauss syndrome), hyper IgE syndrome, Omenn syndrome, some forms of the 22q11 syndrome, rheumatoid arthritis, lupus erythematosus, type I diabetes. Sjogren's syndrome, and bullous pemphigoid.

The object of the invention is also a test kit for the identification of a substance (candidate substance) which inhibits the IgE production, containing:
(a) SWAP-70 and
(b) BCL-6 and/or STAT-6
(c) optionally, regulatory elements of the IgE gene.

For in vitro assays the components (a) and (b) are present in each case as isolated proteins and the optional component (c) as an isolated DNA.

The proteins and the DNA are preferably bound, as described above, to a carrier material or are provided with a marker.

For in sire or in vivo assays, all components (i.e. (a), (b) and optionally (CO are present preferably in a cell or a multicellular organism.

The proteins are preferably also provided here, as described above, with a marker which is selected preferably from affinity tags, haptamers, fluorescent or chemoluminescent biomolecules. The marking occurs here preferably through expression as a fusion protein (protein+marker).

Two markers are preferably selected, as described above, that are suitable for producing a Förster resonance energy transfer (FRET).

BRIEF DESCRIPTION OF THE DRAWINGS

The invention will be explained in the following with the aid of Figures and examples in more detail without being limited thereto:

FIG. 5A shows a FACS analysis of IL-4 stimulated B-cells (B220+) with respect to the BCL-6 expression. FIG. 5B shows the analysis of BCL-6 mRNA with the aid of semi-quantitative RT-PCR. In each case, wt and Swap-70$^{-/-}$ cells with and without IL-4 stimulus, or their mRNA preparations, are compared with each other and related to the charge control HPRT.

DESCRIPTION OF PREFERRED EMBODIMENTS

Materials and Methods

Cell Isolation:

B-lymphocytes were isolated from the spleen of wild type (wt) or Swap-70$^{-/-}$ mice (from 4 to 8 weeks old, C57BL/6) with standard methods and negative selection with MACS beads (Miltenyi Biotec). B-lymphocytes or whole spleen cells (0.3–0.5×10$^6$ cells ml) were cultured in the presence of from 1.6 to 3 ng/ml IL-4 (from X63-IL-4 cell culture supernatant). When noted, the cells were culture on a lawn of L47 fibroblast cells that express CD40L on the surface.

Flow Cytometry:

The flow cytometric detection was carried out with standard methods with anti-mouse CD40R-PE, anti-mouse IgE-FITC (R35-72), anti-mouse IgG1-PE (A85-1), anti-mouse CD45R1B220-PE (RA3-6B2), CD45R/B220-PerCP (RA3-6B2) (BD Biosciences) or anti-mouse IL-4R-biotinylized (R&D System). The Ig production on the surface was measured after stripping (1 min 85 mmol NaCl, 5 mmol KCl, 10 mmol EDTA, 50 mmol NaCH3COO, pH 4.0); phospho-STAT-6 with anti-mouse phospho-STAT-6 (Y641) (J71-773.58.11) (BD Biosciences) used after cell permeabilization (90% methanol) for dyeing.

Real Time RT-PCR:

The detection of IgG1 or IgE mRNA transcription was carried out in CD40L/IL-4-stimulated spleen cells or isolated B-cells by real time RT-PCR. The expression of GAPDH mRNA was measured as a standard. Primers used for the PCR:

| Name | Sequence | Product length | SEQ ID No. |
|---|---|---|---|
| GLTγ1 Fwd | 5'-TCGAGAAGCCTGAGGAATGT-3' | | 3 |
| GLTγ1 Rev | 5'-ATAGACAGATGGGGGTGTCG-3' | 100 bp | 4 |
| GLTϵ, Fwd | 5'-CTGGCCAGCCACTCACTTAT-3', | | 5 |
| GLTϵ, Rev | 5'-CAGTGCCTTTACAGGGCTTC-3' | 100 bp | 6 |
| GAPDH Fwd | 5'-CACAGGACTAGAACACCTGC-3' | | 7 |
| GAPDH Rev | 5'-GCTGGTGAAGACCTCT-3' | 248 bp | 8 |

Immunoblots (1B):

Total protein extracts (total cell extracts), as well as nucleus protein and cytoplasm protein extracts were obtained by means of standard methods from spleen cells or isolated B-cells. The proteins in the obtained protein extracts were separated in each case by means of SDS page and blotted on a nitrocellulose membrane. Used antibodies: anti-GAPDH (monoclonal 6C5, Santa Cruz Biotechnology), anti-JAK1 (rabbit anti-mouse), anti-phospho JAK1 (rabbit anti-mouse, Cell Signaling Technology), anti-STAT-6 (monoclonal YE361), antiphosho-STAT-6 (monoclonal Y641, Abcam), anti-SMC3 (rabbit anti-mouse), anti-Sp1 (rabbit anti-mouse, affinity-purified, Bethyl Laboratories), anty-SWAP-70 (rabbit anti-mouse, affinity-purified).

Immunofluorescence (IF):

The detection of SWAP-70 and STAT-6 protein was cawed out by immunofluorescence in MACS purified B-lymphocytes (1–2×106 cells/m) which were stimulated with IL-4 or IL-4 and CD40L, with anti-STAT-6 (1:100 Abeam) or anti-SWAP-70 (rabbit anti-mouse, affinity-purified 1 and goat-anti-rabbit-Cy3 (1:500) (Dianova) as secondary antibody.

Chromatin Immunoprecipitation (ChIP):

MACS-purified B-lymphocytes (2×10$^6$ cells/ml, from wt or Swap-70$^{-/-}$ mice) were stimulated for 4 hrs. with IL-4 (2 ng/ml) and then after fixation (% of formaldehyde, 10 min, RT) broken down by ChIP buffer (1% SDS, 10 mmol EDTA, 50 mmol Tris HCl, pH 8.1, protease inhibitor cocktail) and ultrasound. After centrifugation a supernatant with DNA fragments in the size of from 100 to 500 bp was obtained. The supernatant was purified with blocked protein A beads (protein A heads agarose beads blocked with 0.2 mg/ml of salmon sperm-DNA and 0.5 mg/ml BSA) and afterwards incubated (4° C. over night) with 1 μg anti-SWAP 70, 2 μg anti-STAT-6 (M20), 2 μg anti-BCL 6 (N-3) or 1 μg rabbit IgG (Santa Cruz Biotech). The thus obtained samples were incubated with blocked protein A beads (4° C., 1 h). The beads were washed and eluted (100 mmol NaHCO3, 1% SDS), incubated for 6 hrs. at 65° C. and treated with proteinase K (1 h, 45° C.). DNA was isolated and PCR with the following primer pairs was carried out:

Iϵ Promoter (I epsilon):

| Name | Sequence | Product length | SEQ ID No. |
|---|---|---|---|
| I epsilon Fwd | 5'-CTAGAAAGAGGCCTACACCTG-3' | | 9 |
| I epsilon Rev | 5'-CCAGACTGTTCTTATTCG-3' | 243b | 10 |

Iγ1 Promoter (I gamma1):

| Name | Sequence | Product length | SEQ ID No. |
|---|---|---|---|
| I gamma1 Fwd | 5'-AGGGGGTGAGGGGGAGTCCA-3' | | 11 |
| I gamma1 Rev | 5'-CCCCCAAAGGCCCAGGTGC-3' | 145 bp | 12 |

CD23 Promoter:

| Name | Sequence | Product length | SEQ ID No. |
|---|---|---|---|
| CD23 Fwd | 5'-TGGCATCGCTGACTCTCCAACA-3' | 118 bp | 13 |
| CD23 Rev | 5'-CTGGGTGGCCACAGCACACA-3' | | 14 |

Control Promoter (without STAT-6 Binding Site):

| Name | Sequence | Product length | SEQ ID No. |
|---|---|---|---|
| Pr Fwd | 5'-TTTGAACTGGAGCTCAGCTGG-3' | | 15 |
| Pr Rev | 5'-TCCATGGTGCTAGCCATATGC-3' | 160 bp | 16 |
| I gamma2a Fwd | 5'-CTGTCACCCACTTTCAATCCTG-3' | | 17 |
| I gamma2a Rev | 5'-GCGTGAAGAAGATTGCTGCTATT-3' | 148 bp | 18 |

Results:

The results of the above discussed tests are summarized as follows:

The cell fractioning of wt or Swap-70$^{-/-}$ spleen cells shows that STAT-6 accumulates as a response to the IL-4 stimulation in the wt nucleus extracts that were produced by salt extraction of isolated nuclei.

Figure 1:
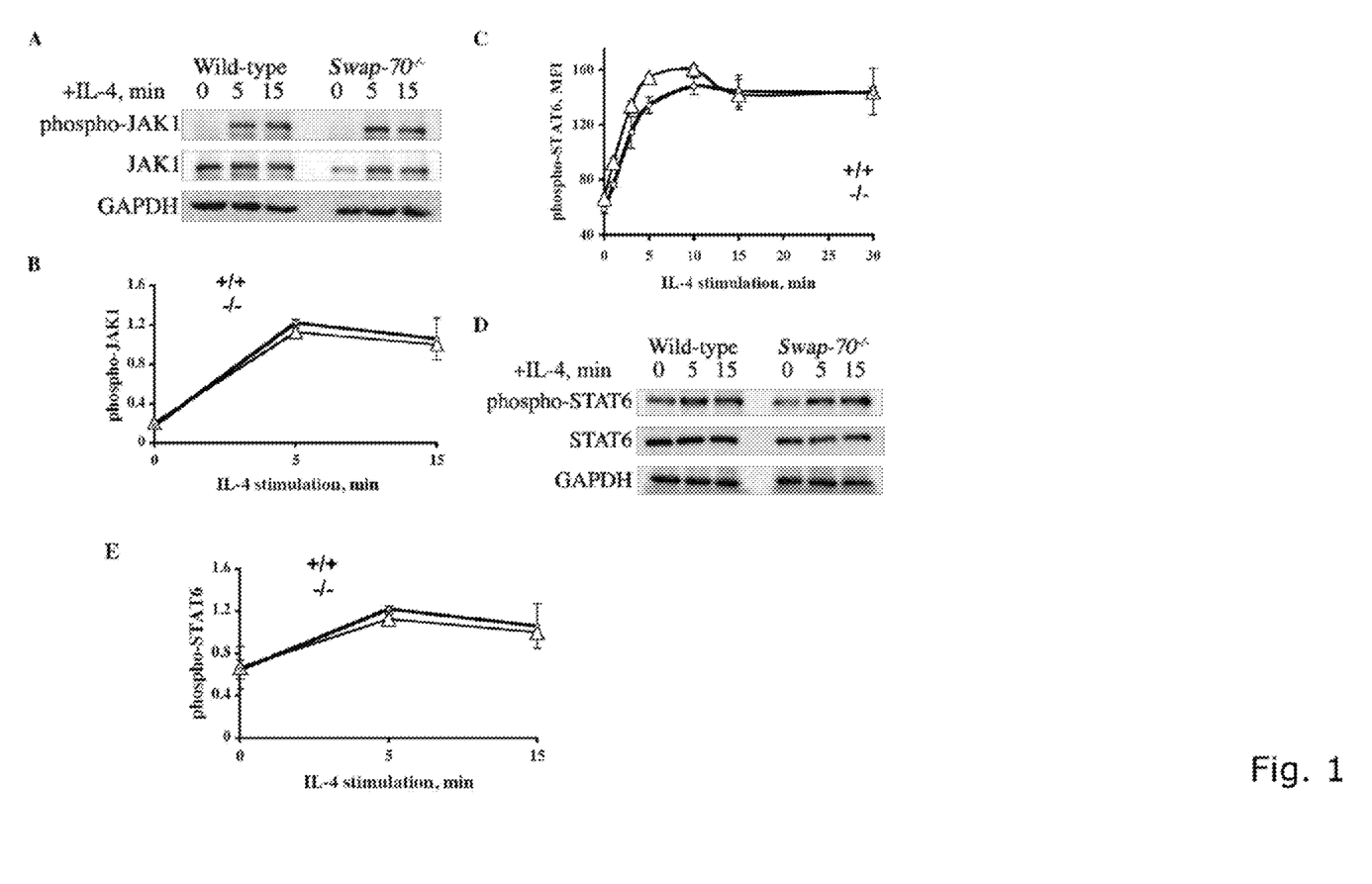
FIG. 1 shows that IL-4 stimulation activates the kinase JAK1 in wild type as well as Swap-70$^{-/-}$ B-cells (FIGS. 1A, 1B), and that STAT-6 is also activated in wild type as well as Swap-70$^{-/-}$ B-cells (FIGS. 1C, 1D, 1E), MFI=medium fluorescence intensity.
Figure 2:
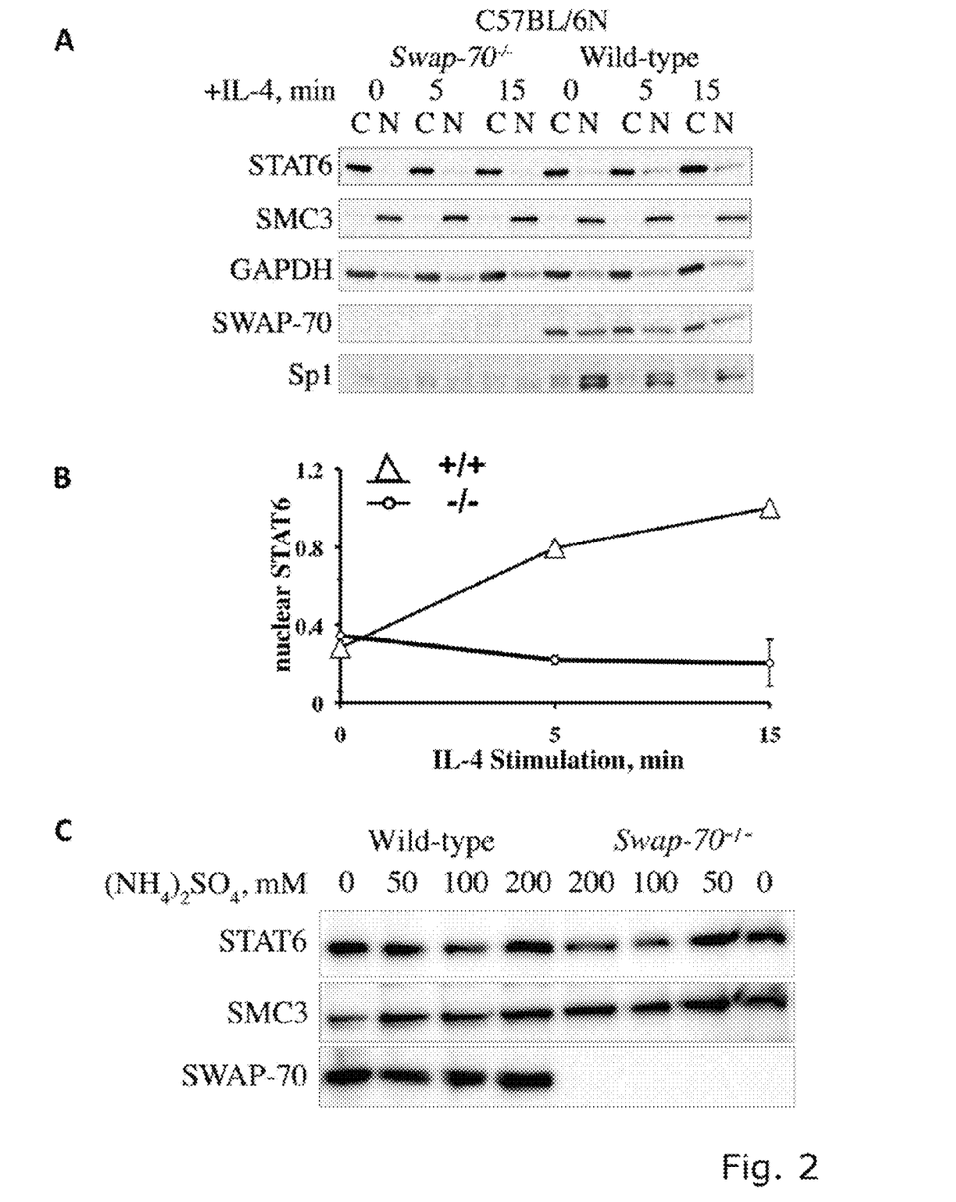
FIGS. 2A and 2B show in Swap-70$^{-/-}$ B-cells the reduced accumulation of STAT-6 in nucleus extracts of the B-cells activated with IL-4. C=cytoplasmic extract, N=nuclear extract; mm minutes of stimulation.
FIG. 2C shows extraction of STAT-6 from nuclei of IL-4 activated B-cells with gradually increasing salt concentration (ammonium sulfate). SMC3 and SWAP-70 serve as comparative proteins. Clearly, less STAT-6 that binds with high affinity, i.e. elutes at high salt concentration, can be extracted from Swap-70$^{-/-}$ B nuclei (200 mmol samples). Sp1=Sp1 transcription factor.
Figure 3:
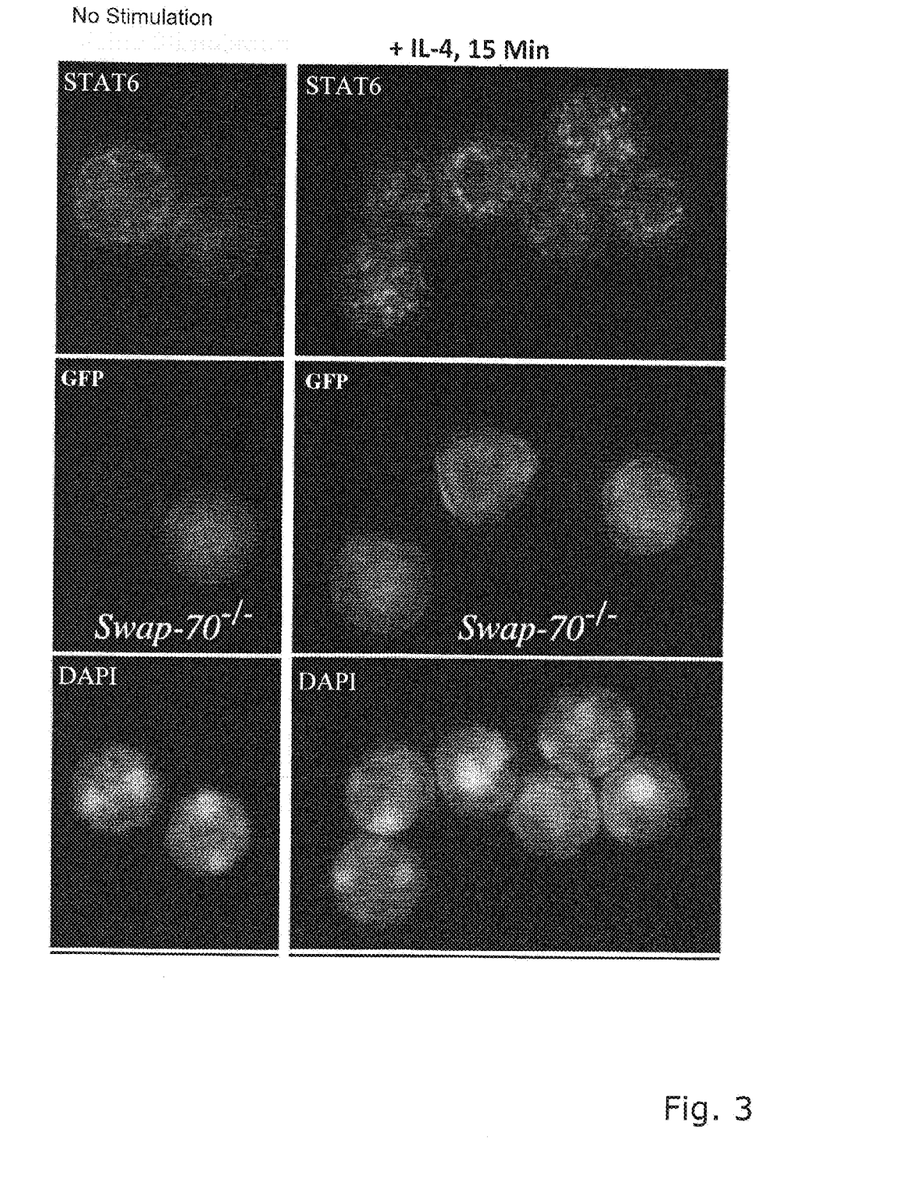
FIG. 3 (fluorescence microscope) shows that the general localization of STAT-6 in the nucleus is not affected. On top: STAT-6; below: DAPI staining of the nuclei; middle: GFP identified Swap-70$^{-/-}$ cells. Wild type and Swap-70$^{-/-}$ cells are present side by side.

However, the nucleus extracts of Swap-70$^{-/-}$ spleen cells contain less STAT-6 than wild type spleen cells (FIGS. 2A, 2B). Like STAT-6 (FIG. 3) SWAP-70 accumulates in the nucleus by stimulation through IL-4 or TL-4 combined with CD40L. The detection of STAT-6 in wt and swap-70$^{-/-}$ B-cells by IF after fixation and permeabilization of the cells ("input") showed no apparent difference between IL-4 activated wild type and Swap-70$^{-/-}$ cells. This may be an indication that STAT-6 can be efficiently translocated into the Swap-70$^{-/-}$ nuclei and therefore be experimentally fixed and made visible therein, but that it does not bind so tightly with the chromatin and therefore is lost in processing of nucleus extracts. From these data one can conclude that STAT-6 shows a low affinity to the Iε promoter in the absence of SWAP-70 and that the presence of SWAP-70 raises this affinity. STAT-6 binds with different affinity to different promoters and binding to Iε requires a high affinity.

In order to measure the strength of the association of STAT-6 with chromatin in the presence or absence of SWAP-70, the inventors have severed cells by Dounce homogenization to avoid leakage, induced by detergents, of loosely bound STAT-6 from the nuclei. Increasing salt concentrations were used to extract proteins sequentially from the nuclei of IL-4 activated splenocytes (FIG. 2C). Comparable fractions of STAT-6 dissociate from the chromatin in the nucleus extract at concentrations of 0 mmol and 50 mmol of ammonium sulfate from wt and Swap-70$^{-/-}$ nuclei. These fractions originate from nucleus plasma STAT-6 which is not bound or bound with low affinity to Chromatin. The amount of STAT-6 which was extracted from Swap-70$^{-/-}$ nuclei by the addition of 200 mmol of ammonium sulfate was however considerably lower than that extracted from wt nuclei. This indicates in general a weaker binding of STAT-6 with chromatin in the absence from SWAP-70. Because binding to Iε requires a high affinity, STAT-6 is apparently significantly reduced at this promoter or is not even present.

Figure 4:
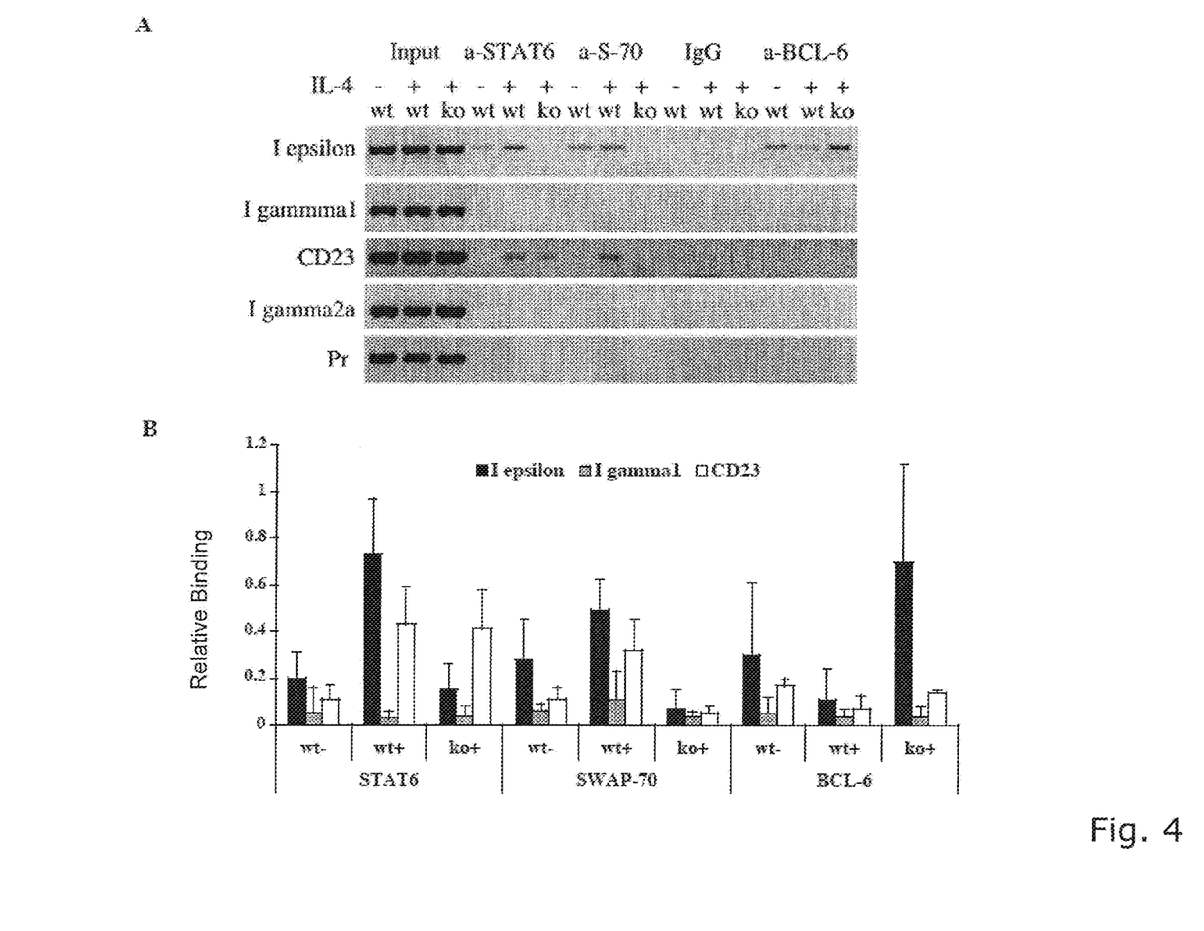
FIGS. 4A and 4B show results of a chromatin immunoprecipitation with anti-STAT 6 (a-STAT-6), anti-SWAP-70 (a-S-70), IgG (control) and anti-BCL-6 (a-BCL-6) after IL-4 stimulation in wild type (wt) as well as Swap-70$^{-/-}$ (ko) B-cells. Input=Chromatin starting material. The results show that in the absence of SWAP-70 clearly more BCL-6 and clearly less STAT-6 are recruited at the Iϵ promoter, as well as that SWAP-70 is recruited substantially independent of the IL-4 stimulation at the Iϵ promoter. 4B shows the quantification of these results.

To prove this, the inventors carried out chromatin immunoprecipitations (ChIP) on wt or Swap-70$^{-/-}$ B-cells which were stimulated with IL-4 by using antibodies against SWAP-70 or STAT-6. Non-stimulated wt B-cells served as a negative control. Primers which are specific for the Iε region with the STAT-6 binding site were used for the semi-quantitative PCR analysis of the DNA that precipitated with SWAP-70 or STAT-6. The results show (FIGS. 4A, 4B) that STAT-6 binds in wild type cells only after IL-4 treatment to the specific 18 promoter region (1 epsilon). In Swap-70$^{-/-}$ B-cells (ko) stimulated with IL-4, binding of STAT-6 with Iε is strongly reduced (FIGS. 4A, 4B). Binding of STAT-6 with Iγ1 (I gamma1) was not detectable; this indicates a weak and/or only passing interaction of STAT-6 with the γ1 promoter. Controls that have promoter regions of IgG2a (I gamma2-Iγ2a) and of a proteasome gene (Pr), with missing STAT-6 binding sites, have generated no PCR signals (FIGS. 4A, 4B). CD23 and the IL4R are known for their transcription under the control by STAT-6. Swap-70$^{-/-}$ B-cells exhibit a normal induction of the CD23 expression as an answer either to IL-4 or CD40 stimulation by CD40L or after treatment with both stimulants as well as an IL-4Rα up-regulation comparable with the wild type. This proves the SWAP-70 independent STAT-6 control of the CD23 and IL4R promoters. Therefore, SWAP-70 regulates primarily the STAT-6 dependent transcription at the Iε promoters. Binding of STAT-6 to the CD23 promoter was tested as a control. In ChIP with wt and Swap-70$^{-/-}$ B-cells a comparable recruitment of STAT-6 at the CD23 promoter was observed (FIGS. 4A, 4B).

CUP with anti-SWAP-70 antibodies a-S-70) proves that SWAP-70 is recruited at 18 promoters in wt cells in IL-4 dependent way (FIGS. 4A, 4B). Therefore, SWAP-70 directly or indirectly binds the Iε promoter.

Figure 5:
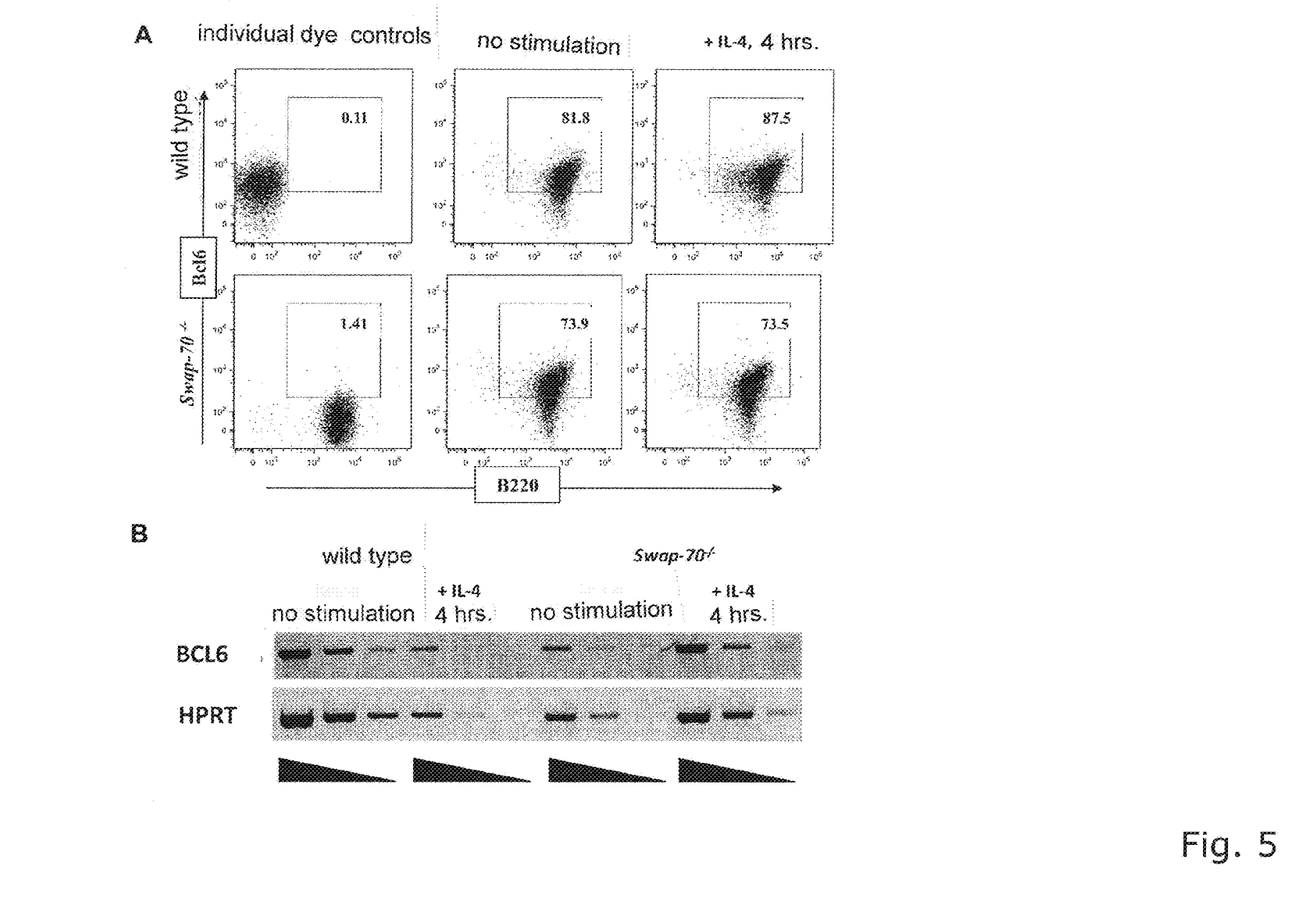
FIG. 5 shows that BCL-6 is expressed in wt and Swap-70$^{-/-}$ B-cells approximately equally.
Figure 6:
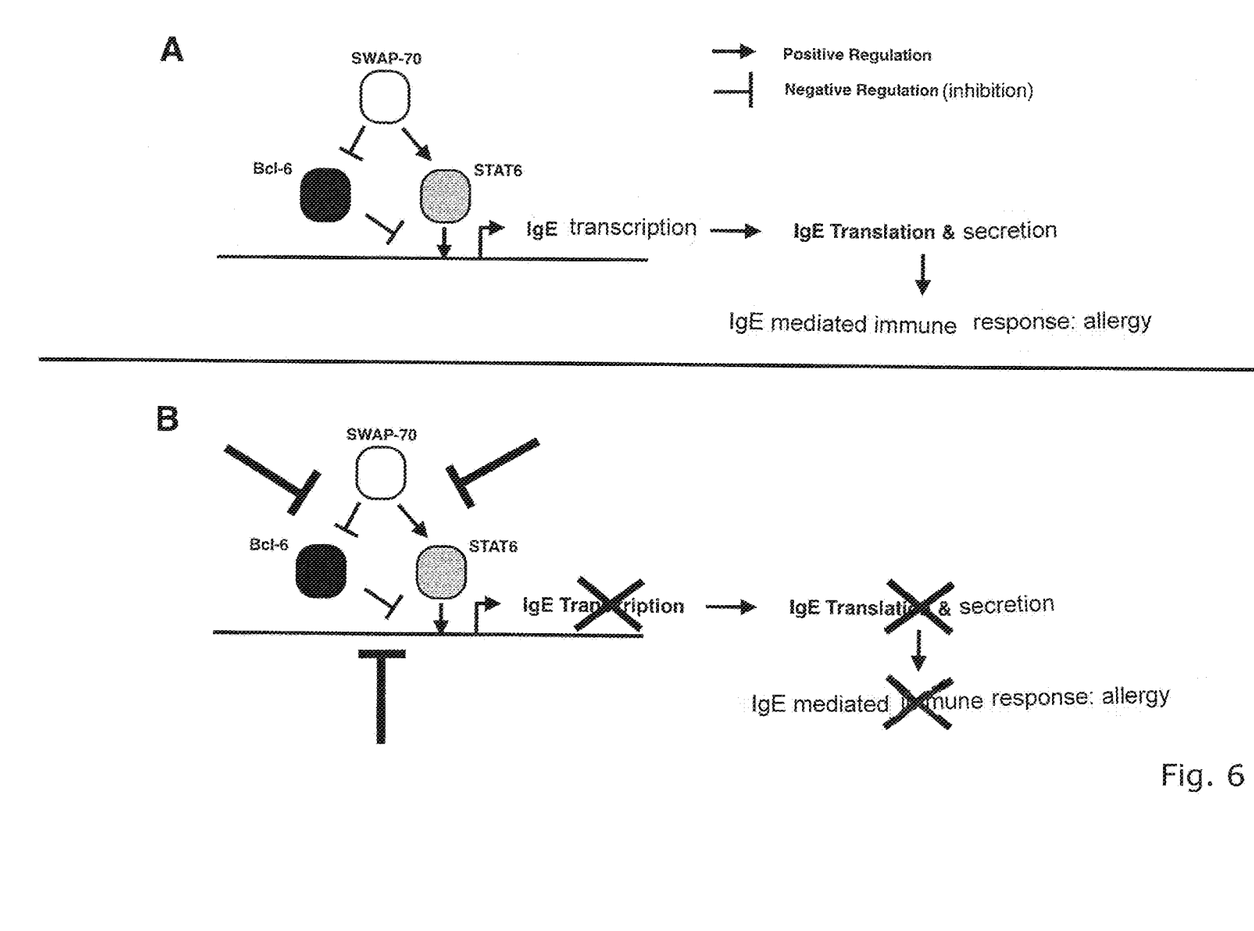
FIG. 6 shows a schematic of the SWAP-70 mediated regulation of the IgE production by influencing the STAT-6/BCL-6 balance. A situation in B lymphocytes after IL-4 stimulation. B: possible starting, points of pharmacological inhibition, shown in the bold-printed inhibition symbol. The cancellation of the SWAP-70 dependent blocking of BCL-6 reinforces the inhibiting effect of BCL-6 on the IgE production. The cancellation of the SWAP-70 dependent stimulation of STAT-6 reduces the stimulating effect of STAT-6 on the NE production.

BCL-6 is known to antagonize binding of STAT-6 to the Iε promoters. BCL-6 and STAT-6 bind to overlapping sequences within Iε promoters. Hence: BLC6 competes with STAT-6 and inhibits the transcription by the recruitment of co-repressors. The inventors determined whether the absence of STAT-6 correlates with a greater presence of BCL-6 at the Iε promoter. While in wt cells ChIP data show reduced BCL-6 binding after IL-4 stimulation, a clearly increased binding of BCL-6 to Iε promoter in IL-4 activated SWAP-70$^{-/-}$ B-cells compared to wt results. Because BCL-6 RNA and protein expression in Swap-70$^{-/-}$ B-cells correspond to that of wt B-cells (FIG. 5), this proves the control of the BCL-6 binding to Iε promoters by SWAP-70.

BCL-6 does not regulate the CD23 transcription. Accordingly, no CD23-specific ChIP signals were Obtained with different anti-BCL-6 antibodies.

All together, the inventors demonstrate herewith that SWAP-70 is required for IL-4 induced ε germline transcription (GLT) wherein SWAP-70 controls the critical balance between BCL-6 and STAT-6 at the Iε promoter. It can be concluded that the interaction of SWAP-70 with BCL-6 and/or the Iε promoter prevents that BCE-6 blocks the STAT-6 mediated induction from εGET. The finding that SWAP-70 is therefore a superior regulator for BCL-6 and STAT-6 in the specific regulation of the IgE production allows to intervene specifically in this new metabolism pathway and to inhibit therefore in a targeted fashion the production of IgE which is a key molecule in allergies and many autoimmune diseases.

What is claimed is:

1. A method for identifying a substance which inhibits IgE production, the method comprising the following:
   (i) contacting:
      (a) at least one candidate substance with
      (b) SWAP-70, bearing an affinity marker or a first molecule suitable for producing Förster Resonance Energy Transfer (FRET), and
      (c) BCL-6 and/or STAT-6, each bearing an affinity marker or a second molecule suitable for producing Förster Resonance Energy Transfer (FRET), the second molecule being different from the first molecule;
   (ii) measuring the interaction of the proteins in vitro or in situ
      by co-precipitation or
      by detecting the Förster Resonance Energy Transfer (FRET),
      and optionally measuring the interaction of the proteins in vitro or in situ with regulatory elements of the IgE gene; and
   (iii) based on the measured interaction of step (ii), selecting a candidate substance which specifically inhibits the interaction between SWAP-70 and STAT-6 and consequently inhibits the SWAP-70 mediated activation of STAT-6 and/or reinforces the interaction between SWAP-70 and BCL-6 and consequently reinforces the BCL-6 mediated inhibition of the SWAP-70 mediated activation of STAT-6.

2. The method according to claim 1, wherein a selected candidate substance inhibits the interaction of SWAP-70 with STAT-6.

3. The method according to claim 1, wherein a selected candidate substance affects the interaction of SWAP-70 with BCL-6 such that the effect of BCL-6 is reinforced.

4. The method according to claim 1, wherein step (i) is carried out in the presence of regulatory elements of the IgE gene to which STAT-6 as well as BCL-6 bind.

5. The method according to claim 4, wherein a selected candidate substance shifts the interaction of STAT-6 and BCL-6 with regulatory elements of the IgE gene in favor of BCL-6.

6. A test kit for identifying a substance which inhibits IgE production, containing components:
   (a) SWAP-70, bearing an affinity marker or a first molecule suitable for producing Förster Resonance Energy Transfer (FRET), and
   (b) BCL-6 and/or STAT-6, each bearing an affinity marker or a second molecule suitable for producing Förster Resonance Energy Transfer (FRET), the second molecule being different from the first molecule;
   (c) optionally, regulatory elements of the IgE gene
   wherein the components (a) and (b) each are present as isolated proteins and the component (c) as isolated DNA.

* * * * *

SEQUENCE LISTING

```
<160> NUMBER OF SEQ ID NOS: 18

<210> SEQ ID NO 1
<211> LENGTH: 88
<212> TYPE: DNA
<213> ORGANISM: Mus musculus

<400> SEQUENCE: 1
cccactgtgc cttagtcaac ttcccaagaa cagaatcaaa agggaacttc caaggctgct      60
aaggccgggg gttcccaccc cacttttta                                         88
```

<210> SEQ ID NO 2
<211> LENGTH: 17
<212> TYPE: DNA
<213> ORGANISM: Mus musculus

<400> SEQUENCE: 2
tgtctcctag aaagagg                                                  17

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
tcgagaagcc tgaggaatgt                                               20

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
atagacagat gggggtgtcg                                               20

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
ctggccagcc actcacttat                                               20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
cagtgccttt acagggcttc                                               20

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
cacaggacta gaacacctgc                                               20

<210> SEQ ID NO 8
<211> LENGTH: 16
<212> TYPE: DNA
<213> ORGANISM: Artificial
<220> FEATURE:
<223> OTHER INFORMATION: Primer

```
<400> SEQUENCE: 8
gctggtgaag acctct                                                    16

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
ctagaaagag gcctacacct g                                              21

<210> SEQ ID NO 10
<211> LENGTH: 18
<212> TYPE: DNA
<213> ORGANISM: Artificial
<220> FEATURE:
<223> OTHER INFORMATION: Primer

<400> SEQUENCE: 10
ccagactgtt cttattcg                                                  18

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11 aggggtgag ggggagtcca                                                 20

<210> SEQ ID NO 12
<211> LENGTH: 19
<212> TYPE: DNA
<213> ORGANISM: Artificial
<220> FEATURE:
<223> OTHER INFORMATION: Primer

<400> SEQUENCE: 12
cccccaaagg cccaggtgc                                                 19

<210> SEQ ID NO 13
<211> LENGTH: 22
<212> TYPE: DNA
<213> ORGANISM: Artificial
<220> FEATURE:
<223> OTHER INFORMATION: Primer

<400> SEQUENCE: 13
tggcatcgct gactctccaa ca                                             22

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
ctgggtggcc acagcacaca                                                20

<210> SEQ ID NO 15
<211> LENGTH: 21
```

```
<212> TYPE: DNA
<213> ORGANISM: Artificial
<220> FEATURE:
<223> OTHER INFORMATION: Primer

<400> SEQUENCE: 15
tttgaactgg agctcagctg g                                     21

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
tccatggtgc tagccatatg c                                     21

<210> SEQ ID NO 17
<211> LENGTH: 22
<212> TYPE: DNA
<213> ORGANISM: Artificial
<220> FEATURE:
<223> OTHER INFORMATION: Primer

<400> SEQUENCE: 17
ctgtcaccca ctttcaatcc tg                                    22

<210> SEQ ID NO 18
<211> LENGTH: 23
<212> TYPE: DNA
<213> ORGANISM: Artificial
<220> FEATURE:
<223> OTHER INFORMATION: Primer

<400> SEQUENCE: 18
gcgtgaagaa gattgctgct att                                   23
```